United States Patent [19]
Borish et al.

[11] Patent Number: 5,851,516
[45] Date of Patent: Dec. 22, 1998

[54] FORMULATION AND APPLICATION METHOD FOR A NEUTRALIZING AGENT IN THE PERMANENT WAVING OF HAIR

[75] Inventors: Edward Borish, Ramsey; Judith A. Cohee, Mahwah, both of N.J.; Andrew Savaides, Norwalk, Conn.

[73] Assignee: Shiseido Co., Ltd., Tokyo, Japan

[21] Appl. No.: 640,099

[22] Filed: Apr. 30, 1996

[51] Int. Cl.$^6$ ..................................................... A61K 7/09
[52] U.S. Cl. ...................... 424/70.1; 424/70.1; 424/70.12
[58] Field of Search ................................ 424/70.1, 70.12, 424/71, 72

[56] References Cited

U.S. PATENT DOCUMENTS

| | | | |
|---|---|---|---|
| 5,093,113 | 3/1992 | Rubinstein et al. | 424/72 |
| 5,352,443 | 10/1994 | Kubo et al. | 424/72 |
| 5,482,704 | 1/1996 | Sweger et al. | 424/70.13 |

*Primary Examiner*—Thurman K. Page
*Assistant Examiner*—D. Faulkner
*Attorney, Agent, or Firm*—Melvin I. Stoltz

[57] ABSTRACT

By providing a neutralizing solution formulated with an alkaline pH, for use with a conventional reducing lotion, a long-lasting, permanently waved head of hair is attained. Furthermore, by employing the neutralizing solution of the present invention, substantially reduced hair damage and substantially improved curl retention and formation is attained. In the preferred embodiment, the alkaline pH neutralizing solution of the present invention is attained by employing a bromate salt in combination with at least one pH adjusting agent. If desired, hair conditioning and wave enhancing additives may also be employed. Preferably, the bromate salt employed comprises one selected from the group consisting of sodium bromate and potassium bromate, with sodium bromate.

13 Claims, No Drawings

FORMULATION AND APPLICATION METHOD FOR A NEUTRALIZING AGENT IN THE PERMANENT WAVING OF HAIR

TECHNICAL FIELD

This invention relates to the art of permanently waving hair, and more particularly, to novel compositions and methods for imparting substantially increased, lasting, durable permanent hair set retention as well as enhanced conditioning sheen and manageability.

BACKGROUND ART

In view of the unique composition of hair fibers and the various changes in style and fashion, the permanent waving of hair has long been of particular interest. In order to best understand the various methods by which hair fibers can be styled or waved, it is important to remember that hair fiber is a proteinaceous material which has many chemical characteristics that relate to manageability, body, texture, static behavior, combability, and sheen. These characteristics may be altered with treatments of surface active agents, salts and polymers such as polysiloxanes, polyoxyalkylenes and polyvinyl pyrrolidones by altering the chemical structure of hair keratin.

It is well known that the three dimensional structure of hair keratin and its stability is related to hydrogen, coulombic, Van der Waals, and disulfide (S—S) bonds which link adjacent protein chains. These forces have also been described as comprising three major bonds that hold the configuration of the hair and are responsible for the strength of the hair. These three bonds are salt linkages, hydrogen bonds, and disulfide bonds. In dealing with these bonds, the hydrogen, coulombic, and Van der Waals forces are weak interactions and are highly dependent upon the water content in the hair keratin. Therefore, only temporary results are obtained by altering these weak interactions.

Because they are so numerous, the hydrogen bonds, involving the amino hydrogen and carbonyl oxygen of the amide linkages, are important. Water, as occurs with moisture in the air (humidity), can weaken these bonds, by becoming a part of a hydrogen bonding structure. However, some of these hydrogen bonds are protected by hydrophobic bonds and will remain even when the hair is wet with water. More powerful hydrogen bond breakers, like high concentration of lithium bromide and urea are required for complete breakage of all hydrogen bonds.

As long as the hair fiber is dry, the strength of the hair fiber is not reduced. For example, a straight hair, wet with water and held by mechanical force in a curly configuration while drying will remain in a curly shape due to the formed hydrogen bonds and salt linkages, and it will not return to its straight shape so long as it remains dry. However, unless mechanically restrained, upon being wet with water, the hair will lose its curly configuration and become straight.

Normal or virgin hair is usually hydrophobic and many of the chemical treatments remove the natural hydrophobic components of hair. This decrease in hydrophobicity causes an increase in hair porosity resulting in increased rate of water absorption. The water-swollen hair is much more susceptible to mechanical stress such as stretching and breaking. Since hair is an elastic structure, the most common problem in hair setting, is the tendency to return to its natural shape. This tendency is highly accelerated under conditions of high humidity. The rate of return of hair into its natural configuration, is dependent on the method of hair deformation used.

Furthermore, when hair is set by the use of water alone, the hair will gradually lose its curly shape through the absorption of atmospheric moisture and the resulting rearrangement of the hydrogen bonds. This is due to the fact that in water, the dominant bonds are disulfide bond, while in the dry state, the dominant bonds are the salt linkages and the hydrogen bonds.

It is well knowN that hair fibers are composed of a unique protein called "keratin" which is distinguished by the fact that it contains a very significant amount of an amino acid (cystine) which contains the element sulfur in addition to the elements nitrogen, oxygen, carbon and hydrogen. In the natural synthesis of hair, the element sulfur covalently links intra or inter polypeptide chains (K) through two sulfur atoms (S—S) to give keratin protein (K—S—S—K). Only by chemical action can this covalent linkage be broken.

Since these disulfide bonds are much stronger than the bonds detailed above and are not affected by water, permanent results are obtained by altering the disulfide bonds through cleavage and recombination. In this way, a permanent configuration change of the hair is attained. However, chemical action is required in order for this disulfide linkage to be broken. In this regard, many prior art compositions have been developed for the cold permanent waving of hair. Typically, these prior art systems treat the hair with reducing agents which break the disulfide (cystine) linkage in the hair, while the hair is wound around a curling rod.

In general, permanent hair waving is usually carried out by subjecting the hair to lotions containing a free —SH group or thiol. These materials are also called mercaptans. In this treatment, the hair usually is either wrapped on the rods with water or the lotion containing the thiol, and then saturated with thiol lotion. The thiol waving agent acts to break the disulfide bonds within the hair fiber forming thiol groups in the hair protein and disulfide bonds between two thiol waving agent molecules. The chemistry involved in the reaction of the mercaptan with the cystine disulfide bonds in the hair fiber is illustrated by the following chemical equations (i), (ii) and (iii):

$$KSSK + RSH \leftrightarrows KSH + RSSK \quad (i)$$

$$RSSK + RSH \leftrightarrows KSH + RSSR \quad (ii)$$

$$KSSK + 2RSH \leftrightarrows 2KSH + RSSR \quad (iii)$$

When a sufficient number of hair disulfide bonds have been broken, the hair is realigned to pair previously unpaired hair protein thiol groups opposite each other. At this point, the hair is rinsed, removing the unreacted thiol waving agent and any water soluble disulfide reaction product formed from it. Then, the hair is saturated with an oxidizing agent, or neutralizer, such as hydrogen peroxide or bromate salt, to reform disulfide bonds between the newly paired hair protein thiols, thereby giving the hair a new configuration or wave, or adding curl to the hair. By rebonding the sites of the reduced keratin in their new curled configuration, a permanent set which is impervious to water is established.

Much of the rebonding of the reduced sites is accomplished by the action of the chemical oxidizing agent, which is typically hydrogen peroxide, and can be illustrated by the following chemical reaction:

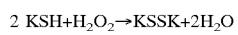

$$2 KSH + H_2O_2 \rightarrow KSSK + 2H_2O$$

In the art of permanent waving, there is much trial and error, with the hair being over-processed, in some instances.

The characteristics of over-processing are raspy feel to the hair or a bleaching of the natural underlying color. Structural evaluation of the hair fiber by instrumentation usually reveals that the structural integrity of the hair is lessened, which is evidenced by either an increase in the amount of cysteine and cysteic acid or a lessening of the cystine content relative to the hair not so processed.

Some detrimental effect to hair fiber is unavoidable, as the process of permanent waving involves controlled bond scission of the disulfide linkages within the keratin proteins. Recovery of these disulfides is the determining factor for the tightness of the curls and overall tensile strength. Typically, in order to reshape hair fibers into a lasting configuration, 20% to 50% of available disulfide bonds must be cleaved and reformed into the new configuration. If insufficient disulfide bonds are broken, the hair fiber will rapidly regain natural configuration.

In spite of the substantial effort that has occurred in the development of various permanent waving composition of this general nature, there has been a general inability to improve the holding power or curl configuration retention of "cold permanent waving" formulations. The typical problem encountered with the use of mercaptan reducing agents for the permanent waving of hair is that the permanency of the curl will not last until it is cut off. Instead, the curl relaxes slowly from the normal wear and tear of every day hair care. In this normal grooming process of shampooing, combing, drying and brushing the hair, the fibers are constantly being put under tension and exposed to forces that oppose the new disulfide and hydrogen bonds that were created in the new curl configuration.

In addition to longer curl retention, the industry has also sought to increase the luster, sheen, gloss and manageability of the hair, as well as provide a permanently waved head of hair which is soft, supple, and possesses a natural feel. However, these goals have not been fully attained.

Furthermore, permanent change in hair keratin coupled with operator error, provides inevitable damage to the hair fibers. This damage is measured by evaluating the tensile strength of hair keratin fibers caused by these chemical treatments. Therefore, it would be advantageous to provide treatments that would produce results of a permanent nature and minimum damage to hair keratin.

Since physical and chemical change in the keratin structure of hair fibers are observed during the deformation and relaxation of hair, researchers have tried to minimize the rate of hair relaxation caused by natural forces and water, utilizing treatments of naturally occurring or synthetic polymers. Some surface polymer treatments have had temporary effect on promoting cohesion and decreasing or retarding the rate of water uptake by the hair fiber, while other treatments have attained temporary improvement of such physical characteristics as sheen, manageability and strength. However, these prior art conditioning agents merely provide a temporary benefit and are incapable of satisfying the long-felt need for substantially permanent hair condition improvement.

Although hydrogen peroxide has become the principal composition employed in neutralizing solutions, hydrogen peroxide has long been known not to be ideal for this purpose. In order to prevent excessive bleaching of hair from hydrogen peroxide, the neutralizing solution must be formulated under acidic conditions. However, even when such acidic compositions are employed, noticeable bleaching of the hair fiber frequently occurs.

As discussed above, the most common neutralizer employed is hydrogen peroxide, which is typically formulated in a solution having a pH of about 4.0. Frequently, when this common prior art neutralizer is applied to the hair after the waving lotion has been applied and removed, an interaction occurs with residual waving lotion product remaining on the hair fiber, causing a bleaching of the hair fiber.

One of the compositions often employed as a substitute for hydrogen peroxide is alkali-metal bromates, typically potassium and sodium bromate. These compositions have been widely demonstrated as highly effective in reforming the disulfide bonds and functioning as an effective neutralizing agent. However, the prior art teaching has required the bromate composition to be preferably formulated at a slightly acidic pH. Generally, the prior art has taught that sodium bromate and potassium bromate at a highly acidic pH is not recommended in order to avoid the formation of bromine.

Although attempts have been made to achieve a neutralizing solution having an alkaline pH, in the same range as most permanent wave lotions, such efforts have failed to produce an effective neutralizing solution. As a result, the prior art has universally taught and employed neutralizers with an acid pH. At best, some neutralizing formulations have approached a pH of 7.0.

Therefore, it is a principal object of the present invention to provide a composition for permanently waving hair fibers and a method for employing a permanent waving composition which is capable of imparting to the head of hair a durable, long-lasting permanent hair set retention.

Another object of the present invention is to provide a permanent wave composition and method of applying a permanent wave composition having the characteristic features described above which is capable of conditioning the hair fibers and improving physical properties of the treated hair such as shine, luster, softness, manageability, hair body, and thickness.

Another object of the present invention is to provide a permanent wave composition and method for applying a permanent wave composition to a head of hair having the characteristic features described above which is capable of imparting a long-lasting permanent wave or setting property to the hair, while substantially reducing hair damage caused during the reduction and oxidation processes.

A further object of the present invention is to provide a permanent wave composition and a method for applying a permanent wave composition to a head of hair having the characteristic features described above which is capable of improving the elastic and tensile properties of the hair fibers.

Another object of the present invention is to provide a neutralizing agent which is formulated with an alkaline pH and is capable of providing the desired reforming of a disulfide bond broken by the permanent wave lotion yielding long-lasting permanent hair set retention.

Other and more specific objects will in part be obvious and will in part appear hereinafter.

DETAILED DESCRIPTION

By employing the present invention, the prior art limitations and difficulties have been overcome and a long-lasting, permanently waved head of hair is attained, using a neutralizing solution formulated with an alkaline pH. In addition, the resulting permanently waved head of hair possesses all of the physical properties, such as shine, luster, softness, manageability, and thickness, which is either equivalent to or better than the results attained using acidic pH neutralizing solutions. Furthermore, by employing the neutralizing solution of the present invention, substantially reduced hair damage and substantially improved curl formation and retention is attained.

In order to provide the desired alkaline pH neutralizing solution in accordance with the present invention, a bromate salt is employed, in combination with at least one pH adjusting agent. If desired, hair conditioning and wave enhancing additives may also be employed. Preferably, the bromate salt employed comprises one selected from the group consisting of sodium bromate and potassium bromate, with sodium bromate being preferred.

As is fully detailed below, the pH of the neutralizing composition of the present invention preferably ranges between about 7 and 10, with a more preferably range being between about 7.3 and 9.5. In Table I, the preferred overall formulation of the neutralizing composition of the present invention is provided.

TABLE I

Neutralizing Composition

| Ingredient | % Wt/Wt |
|---|---|
| Bromate Salt | 5–35 |
| Dibasic Sodium Phosphate | 0–10 |
| Monobasic Sodium Phosphate | 0–2 |
| Ammonium Hydroxide | q.s. to pH |
| Deionized Water | q.s. to 100% |
| pH | 7.3–10 |

As discussed above, the preferred bromate salt is preferably selected from the group consisting of sodium bromate and potassium bromate, and is preferably incorporated in a quantity ranging between about 5% and 18%. If desired, urea may be added to the formulation of the neutralizing composition, in order to assist in penetration into the hair fibers. Furthermore, surfactants may be added for foaming and further penetration, as well as quaternary amines for enhanced conditioning. Finally, carbonates, phosphates, and ammonia based compounds are preferably employed as alkalizing agents.

In Table II, two representative formulations are provided for a neutralizer composition formulated in accordance with the present invention using sodium bromate and no hair enhancing additives. In addition, Table III provides two formulations for a neutralizer composition in accordance with the present invention wherein hair enhancing and conditioning additives are employed. In both Tables II and III, the specific formulations detailed comprise alkaline pH levels at opposed ends of the preferred pH range of the present invention.

TABLE II

Neutralizing Composition

| Ingredient | % Wt/Wt | % Wt/Wt |
|---|---|---|
| Sodium Bromate | 8.000 | 8.000 |
| Dibasic Sodium Phosphate | 0.100 | 0.750 |
| Ammonium Hydroxide | — | 0.020 |
| Deionized Water | q.s. to 100% | q.s. to 100% |
| pH | 7.3 | 9.55 |

TABLE III

Neutralizing Composition

| Ingredient | % Wt/Wt | % Wt/Wt |
|---|---|---|
| Sodium Bromate | 8.000 | 8.000 |
| Urea | 9.000 | 9.000 |
| Sodium Hydroxymethyl Glycinate | 0.200 | 0.200 |
| Polyquaternium 22 | 2.000 | 2.000 |
| Lecithin | 0.010 | 0.010 |
| Monobasic Sodium Phosphate | 0.500 | — |
| Dibasic Sodium Phosphate | 1.400 | 2.500 |
| Disodium MIPA Cocamidosulfosuccinate | 5.000 | 5.000 |
| Polysorbate 80 | 1.500 | 1.500 |
| Ammonium Hydroxide | — | 0.040 |
| Deionized Water | q.s. to 100% | q.s. to 100% |
| pH | 7.3 | 9.46 |

By employing a neutralizing or oxidizing composition in accordance with the present invention which has a pH ranging between about 7.3 and 10, long-lasting permanently waved hair is attained with the hair fibers having physical properties substantially better than is attained with prior art acid based oxidizers. In particular, substantially less hair damage is found with the present invention, while improved curl retention and formation is provided.

BEST MODE FOR CARRYING OUT THE INVENTION

In order to substantiate the versatility and substantial hair enhancements achieved by employing alkaline neutralizing compositions of the present invention, as well as by employing the methods of application of this invention, the following examples are presented. In the following disclosure, the universal applicability of this invention is fully detailed, along with the ability of the neutralizing composition of the present invention to permanently wave hair with substantially improved, long-lasting, physical enhancements and characteristics permanently formed therein. It is to be understood, however, that these examples are intended as a teaching of the best mode for carrying out the present invention and are not intended to limit, in any manner, the breadth of this discovery.

In order to prove the efficacy of the present invention and clearly establish that neutralizing compositions having an alkaline pH are effectively used to provide permanent hair waving results better than, or at least equivalent to, the results attained with prior art acidic neutralizing compositions, the following tests were conducted. In each of the following tests, a neutralizing composition formulated with sodium bromate as the principal active ingredient was prepared. In Table IV, the specific formulation of this neutralizing composition is fully detailed.

TABLE IV

Bromate Neutralizer

| Ingredients | Amount |
|---|---|
| Sodium Bromate | 8.0 g |
| Urea | 9.0 g |
| Polyquaternium - 22 | 2.0 g |
| Dibasic Sodium Phosphate | 2.0 g |
| Sodium Hydroxymethylglycinate | 0.2 g |
| Water | q.s. to 100 ml |
| pH | 8.0 |

In addition, a neutralizing composition formulated using hydrogen peroxide was prepared and employed throughout the following tests as a comparison for the efficacy of the bromate neutralizer. In Table V, the specific composition of the hydrogen peroxide neutralizer is detailed.

TABLE V $H_2O_2$ Neutralizer

| Ingredients | % Wt./Wt. |
|---|---|
| Water | 93.21 |
| Methylparaben | 0.2 |
| Dicetyldimonium Chloride | 1.1 |
| Cetyl/Stearyl Alcohol | 0.2 |
| Ceteth-20 | 0.16 |
| Dimethicone | 0.30 |
| $H_2O_2$ (50%) | 4.80 |
| Dibasic Sodium Phosphate | 0.02 |
| Phosphoric Acid | 0.01 |
| pH | 4.0 |

In order to effectively compare the performance of the bromate neutralizer with the performance of the hydrogen peroxide neutralizer, a conventional permanent waving lotion was employed as part of the permanent wave process for both the bromate neutralizer and the hydrogen peroxide neutralizer. In each of the tests conducted, and detailed below, the permanent wave lotion detailed in Table VI was employed.

TABLE VI

| Ingredient | Amount |
|---|---|
| PERMANENT WAVE LOTION Part A | |
| Water | 90 ml |
| Methyl paraben | 0.05 g |
| $H_2O_2$ (50%) | 6.50 g |
| Dibasic Sodium Phosphate | 0.022 g |
| Phosphoric Acid | 0.028 g |
| Water | q.s. to 100.0 ml |
| pH | 4.0 |
| PERMANENT WAVE LOTION Part B | |
| Ammonium Thiolactate | 8.76 g |
| MEA Thiolactate | 5.84 g |
| Monoethanolamine (MEA) | 2.0 g |
| Tetrasodium Etidronate | 0.05 g |
| Ammonium Bicarbonate | 0.2 g |
| Nonoxynol-15 | 1.5 g |
| Fragrance | 0.75 g |
| Dow Corning 939 | 1.5 g |
| Water | q.s. to 100.0 ml |
| pH | 8.5 |
| FINAL PERM SOLUTION | |
| Part A | 18.2 ml. |
| Part B | 80 ml. |

EXAMPLE 1

In order to demonstrate the efficacy of the present invention and compare the performance attained using the present invention to conventional hydrogen peroxide neutralizers, numerous hair fibers classified as normal hair were treated with the permanent wave lotion defined in Table VI and then neutralized using either the bromate neutralizer detailed in Table IV or the hydrogen peroxide neutralizer detailed in Table V. In each instance the hair fibers were processed with the permanent wave lotion defined in Table VI for 20 minutes with the lotion having a temperature of 37° C. Then, the permanent wave lotion was removed by rinsing the hair fibers for one minute.

Following the rinsing, one group of the hair fibers were saturated with the bromate neutralizer for 10 minutes, while the remaining hair fibers were saturated with the hydrogen peroxide neutralizer for 5 minutes. At the completion of this permanent waving procedure, the 20% index of the hair fibers were measured.

As is well known, the 20% index is the measure of hair fiber damage in the yield region and is defined as the force ratio of treated to untreated hair fiber at 20% elongation. This method is commonly used to evaluate the overall damage caused to hair fibers.

By referring to Table VII, the results attained from this test are provided as an overall average from the various test samples. Furthermore, as shown in Table VII, each of the hair fibers were subjected to a total of three separate and independent permanent wave procedures, with the 20% index being determined after each perm application. In this way, the increased damage caused by multiple perming was determined.

TABLE VII

20% Index for Multiple Perm Applications

| Number of Perms | Perm Lotion/Bromate Neutralizer | Perm Lotion/Peroxide Neutralizer |
|---|---|---|
| 1 | 0.842 ± 0.046 | 0.826 ± 0.086 |
| 2 | 0.730 ± 0.050 | 0.718 ± 0.050 |
| 3 | 0.672 ± 0.043 | 0.598 ± 0.066 |

In order to effectively measure the tensile strength of the hair, an Instron Apparatus Model 1120 was used with each of the samples detailed above, with the resistant forces for each of the hair fibers being determined at 20% elongation under aqueous immersion conditions. The overall results attained from this elongated test are shown in Table VII. The values presented in this table represent the final reading (after treatment) divided by the initial reading. As a result, values closest to one indicate stronger relative tensile properties and less damage.

As is evident from the results attained from this test and detailed in Table VII, the 20% index resulting from the use of the bromate neutralizer with a pH of 8.9 was substantially better than the 20% index attained by the hair fibers on which the hydrogen peroxide neutralizer (pH=4) was employed. As a result, the use of the bromate neutralizer of the present invention produced substantially less damage to the hair fibers as compared to the results attained from conventional hydrogen peroxide neutralizers.

EXAMPLE 2

Using hair fibers which were permanently waved as detailed above in Example 1, hair fibers were tested to determine protein loss resulting from the permanent wave application utilizing the method according to S. S. Sandhu and C. R. Robbins, *J. Soc. Cosmet. Chem.*, 44, 163–175 (1993). As a comparison, protein loss was also measured on hair fibers which were not permed. The results attained from these tests are shown as an average in Table VIII.

An increase in the protein loss measurement above that of unpermed hair represents a measure of damage caused to the hair by the permanent waving process. If no damage were caused to the hair, protein loss increase would be zero.

TABLE VIII

| Hair Treatment | mg Protein/g Hair |
| --- | --- |
| Perm Lotion/Peroxide Neutralizer | 32.28 ± 1.07 |
| Perm Lotion/Bromate Neutralizer | 20.90 ± 1.25 |
| Unpermed | 12.89 ± 1.41 |

As is evident from a review of the results detailed in Table VIII, the bromate neutralizer caused substantially less damage to the hair fiber than the peroxide neutralizer. In particular, when the protein loss evident in the unpermed hair fiber is compared to the protein loss resulting from the use of a bromate neutralizer, substantially little additional damage was caused. However, it is evident that the peroxide neutralizer substantially increased the damage caused to the hair fibers.

EXAMPLE 3

A further test which was conducted to evaluate the damage caused to the hair fibers due to the permanent waving is the measure of the increased water retention of the hair fiber. Increased water retention is the measure of the damage caused to the hair fiber by increased porosity.

In conducting this evaluation, each of the hair fibers were initially tested for porosity in the unpermed state, by having the water retention of the hair fibers determined. This procedure consisted of drying the fibers overnight to a constant weight at ambient temperatures and 65% relative humidity, dipping them in deionized water for one hour and removing the excess water by centrifuging at 2000 rpm for 2 minutes. The fibers were then reweighted and the % water retention calculated was made as follows:

$$\% \text{ Water Retention} = \frac{\text{Wet Hair Weight} - \text{Dry Hair Weight}}{\text{Dry Hair Weight}} \times 100$$

Thereafter, the hair fibers were permanently waved, in the manner detailed above in Example 1, and the permanently waved hair fibers were tested again for water retention. The results of these tests are shown in Table IX as percent water retention. This result was obtained by subtracting the unpermed measurement from the permed measurement and dividing the result by the unpermed measurement.

TABLE IX

WATER RETENTION

| Hair Treatment | % |
| --- | --- |
| Perm Lotion/Bromate Neutralizer | 32.69 ± 1.96 |
| Per Motion/Peroxide Neutralizer | 32.86 ± 0.72 |
| Unpermed | 17.03 ± 0.39 |

As is evident from the results provided in Table IX, the bromate neutralizer and the peroxide neutralizer performed substantially identically to each other. For comparative purposes, measurements were also taken on hair fibers which were unpermed.

EXAMPLE 4

A further test conducted in order to determine the damage to the hair fibers consisted of measuring the cysteic acid formation in the permed hair fibers. A measure of increased cysteic acid is an indication that hair fibers have been weakened and damaged. Ideally, zero cysteic acid would be found and, as a result, the greater quantity of cysteic formed the more weakened the hair fiber has become. In order to measure the cysteic acid formation, the following test procedure was employed. Fibers were analyzed using a modification of the method of S. Moore and W. H. Stein, *Methods Enzymology*, 6 (1963) p.819 employing 6N HCl/0.05% mercaptoethanol for hydrolysis.

In Table X, the results attained from this test procedure are provided. For comparative purposes, the cysteic acid found in unpermed hair was also measured.

TABLE X

Cysteic Acid Formulation

| Hair Treatment | ($\mu$Moles Cysteic Acid/g Hair) |
| --- | --- |
| Unpermed | 22.82 ± 0.62 |
| Bromate | 35.24 ± 0.40 |
| Peroxide | 60.25 ± 0.19 |

As is evident from a review of the data detailed in Table X, the permanent wave process using the bromate neutralizer provided substantially reduced levels of cysteic acid. As a result, hair permed with the bromate neutralizer of this invention was substantially less damaged and less weakened, than hair permanently waved using the hydrogen peroxide neutralizer. In particular, when the level of cysteic acid formed is compared to the amount of cysteic acid found in unpermed hair, very little increased damage was caused to the hair fibers when the bromate neutralizer was employed.

EXAMPLE 5

In order to provide further evidence of the superior performance attained by permanently waving hair using the bromate neutralizer of the present invention, tests were conducted using the permanent waving formulation defined in Table XI as the reducing agent in combination with each of the bromate neutralizers detailed in Tables II and III.

TABLE XI

PERM FORMULATION
TINTED

| INGREDIENT | % W/V |
| --- | --- |
| Ammonium Thiolactate (100%) | 98.4 |
| Dithiodilactic Acid | 1.05 |
| Monoethanolamine 99% | 1.70 |
| Ammonium Bicarbonate | 1.00 |
| Tetrasodium Etidronate | 0.05 |
| Hydrolyzed Wheat Protein | 0.01 |
| Nonoxynol-15 | 2.00 |
| Fragrance | 1.00 |
| Amodimethicone | 1.50 |
| Styrene/Acrylate Copolymer | 0.50 |
| Deionized Water | q.s. to 100% |

In conducting these tests, the test tube curl procedure (TTTC) was used for each of the bromate neutralizers at their respective pH levels.

In following this procedure, twelve freshly shampooed human hair fibers were knotted at the root end and cut to a length of 3.5 inches from the knot. The bundle was immersed in water and then wound around an aluminum mandrel having a diameter of 6.5 millimeters. The mandrel was placed in a test tube containing 5 milliliters of the reducing solution and the test tube was capped with Parafilm and immersed into a water bath maintained at a constant temperature of 37° C. for 10 minutes. Once completed, the permanent wave lotion was drained off, and the test tube and its contents were rinsed with running water for two minutes.

After rinsing, 10 milliliters of the particular bromate neutralizer was added to the test tube and the hair fibers were immersed in the bromate neutralizer and retained totally submerged for one minute. Then, the hair fibers were removed and allowed to stand at room temperature for nine minutes. Thereafter, the hair fibers were rinsed with running water for two minutes.

Following the rinsing, the hair fibers were unwound from the aluminum mandrel and the obtained curl was immersed in water. Then, both the length of the hair fiber and the diameter of the resulting hair coil were recorded. In addition, the 20% index was also determined in the manner detailed above in reference to Example 1. The results attained from this test are detailed in Table XII.

TABLE XII

| Neutralizer Used | Diameter | Length | 20% Index |
|---|---|---|---|
| Bromate Neutralizer (Table II) pH 7.3 | 8.28 ± .37 | 31.9 ± 3.9 | .796 ± .02 |
| Bromate Neutralizer (Table II) pH 9.55 | 7.63 ± .28 | 31.7 ± 2.6 | .791 ± .07 |
| Bromate Neutralizer (Table III) pH 7.3 | 7.98 ± .04 | 24.4 ± 3.9 | .825 ± .05 |
| Bromate Neutralizer (Table III) pH 9.5 | 7.78 ± .13 | 25.7 ± 1.5 | .760 ± .05 |

As is evident from the data provided in Table XII, each of the bromate neutralizer formulas produced substantially similar results, with each result providing a highly desirable and effective permanently waved hair.

EXAMPLE 6

In order to demonstrate the efficacy of the present invention in providing long-lasting curl retention, wave longevity tests were conducted on different types of tinted hair. In these tests, hair fibers were permanently waved using the reducing lotion and process defined in Example 5 and Table XI on tinted hair and the reduction lotion defined by Table XIII on hilift tinted hair. Each of these reducing lotions were employed in combination with the bromate neutralizer defined in Table III. Upon completion of the permanent wave process, crest-to-crest measurements were taken.

TABLE XI

PERM FORMULATION
HILIFT TINT, HIGHLIGHT & BLEACHED HAIR

| INGREDIENT | % W/V |
|---|---|
| Ammonium Thiolactate (100%) | 98.4 |
| Dithiodilactic Acid | 2.10 |
| Monoethanolamine 99% | 1.80 |
| Ammonium Bicarbonate | 1.00 |
| Tetrasodium Etidronate | 0.05 |
| Hydrolyzed Wheat Protein | 0.01 |
| Nonoxynol-15 | 2.00 |
| Fragrance | 1.00 |
| Amodimethicone | 1.50 |
| Styrene/Acrylate Copolymer | 0.50 |
| Deionized Water | q.s. to 100% |

Once the initial measurements were completed, all of the hair fibers were held at high humidity (98.5%) and high temperature (96.5° F.) for 48 hours. Then, further crest-to-crest measurements were taken.

In Table XIV, the average results attained for this test procedure are provided along with the actual percent change for each hair type and for each neutralizing solution. As is evident from the data, hair fibers permanently waved with the bromate neutralizer of the present invention provided highly effective, long-lasting permanent wave results.

TABLE XIV

| Hair Type | Bromate Neutralizer (Table III) pH 7.3 | | | Bromate Neutralizer (Table III) pH 9.5 | | |
|---|---|---|---|---|---|---|
| | Initial | 48 Hrs. | % | Initial | 48 Hrs. | % |
| Tinted | 0.975 | 1.200 | 19% | 0.850 | 1.100 | 23% |
| Hilift Tint | 0.975 | 1.000 | 2.5% | 0.827 | 0.855 | 3.5% |

It will thus be seen that the objects set forth above, among those made apparent from the preceding description, are efficiently attained and, since certain changes may be made in carrying out the above methods and in the composition set forth without departing from the scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Particularly, it is to be understood that in said claims, ingredients or compounds recited in the singular are intended to include compatible mixtures of such ingredients wherever the sense permits.

Having described our invention, what we claim as new and desire to secure by Letters Patent is:

1. A neutralizing or oxidizing composition for application to hair as part of a permanent waving process, said composition comprising:

A. between about 5% and 35% by weight of a bromate salt;

B. between about 0% and 10% by weight of dibasic sodium phosphate;

C. between about 0% and 2% by weight of monobasic sodium phosphate;

D. ammonium hydroxide in a quantity sufficient for maintaining the pH of the final composition in a range between about 7.3 and 10; and E. deionized water forming the balance;

whereby a neutralizing or oxidizing composition is attained having an alkaline pH which is capable of being effectively employed as part of a permanent waving process.

2. The neutralizing or oxidizing composition defined in claim 1, wherein the bromate salt comprises between about 5% and 18% by weight of the total composition.

3. The neutralizing or oxidizing composition defined in claim 2, wherein said bromate salt comprises one selected from the group consisting of sodium bromate and potassium bromate.

4. The neutralizing or oxidizing composition defined in claim 3, wherein said bromate salt comprises sodium bromate.

5. A neutralizer or oxidizing composition for application to hair as part of a permanent waving process, said composition comprising:

A. between about 5% and 18% by weight of sodium bromate;
B. between about 0.1% and 5% by weight of dibasic sodium phosphate;
C. between about 0% and 2% by weight of monobasic sodium phosphate;
D. ammonium hydroxide in sufficient quantity to maintain the pH of the final composition at between about 7.3 and 9.6; and
E. deionized water forming the balance.

6. The neutralizing or oxidizing composition defined in claim 5, wherein said composition further comprises:
F. about 9% by weight of urea;
G. about 0.2% by weight of sodium hydroxymethyl glycinate; and
H. about 2% by weight of polyquaternium-22.

7. The neutralizing or oxidizing composition defined in claim 6, and further comprising:
I. about 0.01% by weight of lecithin;
J. about 5% by weight of disodium MIPA cocamidosulfosuccinate; and
K. about 1.5% by weight of polysorbate-80.

8. A process for permanently waving hair by performing conventional steps to reduce the hair and to rinse the reducing solution from the hair, followed by the steps of:
A. saturating the reduced hair with a neutralizing or oxidizing composition comprising a pH ranging between about 7.3 and 10; and
B. rinsing the neutralizing composition from the hair.

9. The process defined in claim 8, wherein the neutralizing composition is further defined as comprising:
A. between about 5% and 35% by weight of a bromate salt;
B. between about 0% and 10% by weight of dibasic sodium phosphate;
C. between about 0% and 2% by weight of monobasic sodium phosphate;
D. ammonium hydroxide in a quantity sufficient for maintaining the pH of the final composition in a range between about 7.3 and 10; and
E. deionized water forming the balance.

10. The process defined in claim 9, wherein said bromate salt comprises sodium bromate.

11. The process defined in claim 8, wherein the neutralizing composition is further defined as comprising:
A. between about 5% and 18% by weight of sodium bromate;
B. between about 0.1% and 3% by weight of dibasic sodium phosphate;
C. between about 0% and 3% by weight of monobasic sodium phosphate;
D. ammonium hydroxide in sufficient quantity to maintain the pH of the final composition at between about 7.3 and 9.6; and
E. deionized water forming the balance.

12. The process defined in claim 11, wherein the neutralizing composition further comprises:
F. about 9% by weight of urea;
G. about 0.2% by weight of sodium hydroxymethyl glycinate; and
H. about 2% by weight of polyquaternium-22.

13. The process defined in claim 12, wherein the neutralizing composition further comprises:
I. about 0.01% by weight of lecithin;
J. about 5% by weight of disodium MIPA cocamidosulfosuccinate; and
K. about 1.5% by weight of polysorbate-80.

* * * * *